United States Patent [19]

Sillard

[11] Patent Number: 5,503,557
[45] Date of Patent: Apr. 2, 1996

[54] APPARATUS FOR REMOVABLY SECURING A DENTAL PROSTHESIS

[76] Inventor: Rannar Sillard, 206 Madison Ave., Lakewood, N.J. 08701

[21] Appl. No.: 274,236

[22] Filed: Jul. 13, 1994

[51] Int. Cl.⁶ .......................... A61C 13/12; A61C 13/225
[52] U.S. Cl. .......................... 433/172; 433/173
[58] Field of Search .................. 433/172, 173, 433/174, 175, 176

[56] References Cited

U.S. PATENT DOCUMENTS

| | | | |
|---|---|---|---|
| 4,884,970 | 12/1989 | Mays | 433/173 X |
| 4,904,186 | 2/1990 | Mays | 433/173 X |
| 4,931,016 | 6/1990 | Sillard | 433/173 X |
| 5,057,017 | 10/1991 | Sillard | 433/173 X |

Primary Examiner—Nicholas D. Lucchesi
Attorney, Agent, or Firm—Clifford G. Frayne

[57] ABSTRACT

A releasable holding element for the attachment of a primary support bar of a full or partial dental prosthesis to the overlaid secondary support bar and artificial teeth, the releasable holding element in the form of a latch pin, elongated in shape, being utilized as the actual electrode for forming the channel for its ultimate receipt in the primary and secondary support bars, the receiving channel forming an acute angle with the axis of the primary support bar and secondary bar in order to provide greater contact area between the releasable holding element and the primary bar and secondary bar.

7 Claims, 3 Drawing Sheets

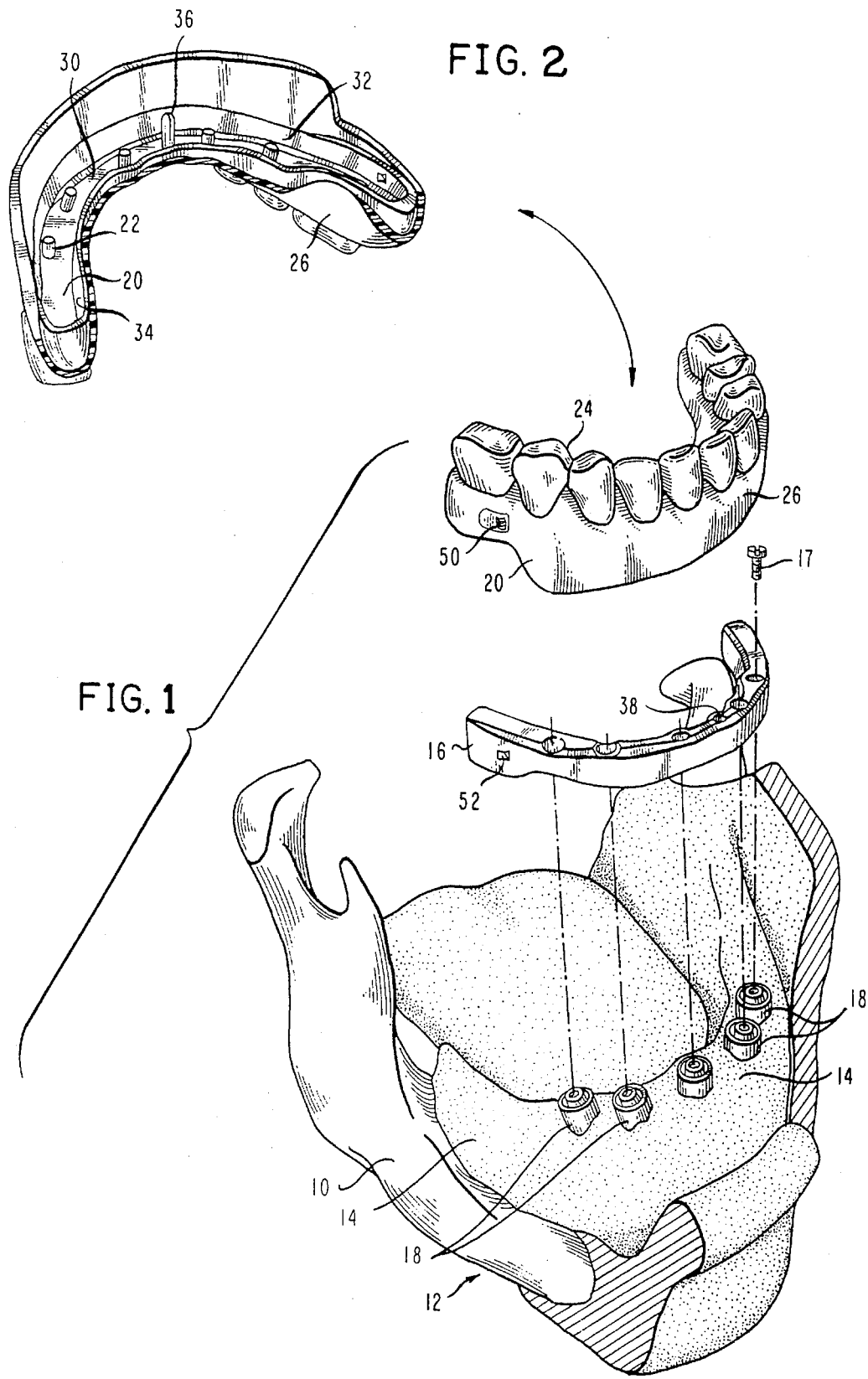

APPARATUS FOR REMOVABLY SECURING A DENTAL PROSTHESIS

BACKGROUND OF THE INVENTION

1. Field of the Invention

The present invention relates to dental prosthesis and, in particular, dental implant prosthesis and an apparatus and method for making same which removably secures the artificial teeth portion to the underlying support of a partial or full dental prosthesis.

2. Description of the Prior Art

In the area of dental prosthetics, there have been primarily two major types of dental implant prosthetics which have been in use. The first, commonly known as the overdenture, provides for support structure to be implanted in the alveolar bone, which support structure extends above the gum line and permits the patient to snap-fit the denture in place. This type of construction permits the patient to remove the denture himself and clean the denture and gum area. The drawback of an overdenture is that it does not normally provide sufficient stability under all eating or chewing conditions.

The second type of prosthesis in wide use is that of the fixed prosthesis. Again, a support structure is anchored in the alveoloar bone, the support structure extending above the gun line and the prosthesis being permanently secured through the support structure into the bone. This type of denture normally provides a more stable denture for the patient, but aesthetic and hygiene problems arise in that the denture can only be removed by a dentist to permit cleaning in the area under the prosthesis and proximate to the support structure.

Applicant, in his prior patent, U.S. Pat. No. 4,931,016 disclosed an apparatus and method for making a fixed, removable dental prosthesis which the individual could remove for cleaning of the prosthesis and the underlying gum area. The prosthesis disclosed in the aforementioned patent provided the necessary stability for all eating and chewing conditions, but allowed the individual to remove the prosthesis for cleaning thereby eliminating the need for a dental visit.

Applicant has further refined the aforesaid dental implant system with the development of a novel latching attachment which secures the supra structure of the prosthesis which contains the secondary support bar and artificial teeth, to the underlying primary support bar. This novel latching attachment provides for greater strength in the attachment process and further secures the stability of the prosthesis under all eating and chewing conditions.

The secondary support bar and the primary support bar are fitted together in accordance with the teachings of Applicant's aforesaid U.S. Pat. No. 4,921,016. A latching mechanism is normally provided on the interior rear portion of the prosthesis to allow the user to remove the secondary support bar and overlying artificial teeth for cleaning as well as to permit cleaning of the gum area about the primary support bar. The usual manner of preparing the latch was to form an opening perpendicular to the primary and secondary support bars, in a horizontal axis and to then fit a rotatable clip in the aperture which could be twisted to a locked position to an unlocked position thereby allowing the removal of the secondary support bar and overlying prosthesis. These twist-lock clips secure the denture in two places in the rear of the mouth. The secondary support bar had sufficient downwardly depending detentes, cooperative with apertures in the primary support bar to prevent the secondary support bar and overlying prosthesis from moving in a horizontal plane with respect to the primary support bar. However, a significant amount of stress is placed on the prosthesis during the eating process, which stress attempts to vertically separate the secondary support bar and overlying denture or prosthesis from the primary support bar. The aforementioned twist-lock clips were the sole means for preventing this vertical separation with the exception of the frictional engagement between the secondary support bar and the primary support bar.

Certain of the problems associated with the twist-lock clip were inherent in the sparking erosion of their receptacle through the electrical discharge method.

In spark eroding the aperture for the securing mechanism, the electrode can cause three basic problems which do not permit the tight fit of a securing means. The first undesirable property is that of overcut. This is the tendency of the electrode to erode or cut an aperture slightly larger than itself. This occurs because of previously eroded material passing along the sides of the electrode for removal and causing additional erosion to the work piece as they pass.

The second undesirable property is taper caused by the same particles or residue being flushed from the bottom of the eroded hole. These particles continue to create discharge as they pass along the surfaces causing more metal to be removed in these areas. Flushing or suction is utilized to minimize this property, but it nevertheless exists.

The third property is the inability to obtain squared corners at the butt end of recesses. This is caused by a higher concentration of flux or discharges at the corner edge of the electrode, thus causing a rounded corner or edge at the butt end of the recess.

These three factors contribute to the difficulty in obtaining a tight, secure fit for the securing mechanism for the dental prosthesis. They contribute to the introduction of a slight play in the twist-lock clip which over time may cause wear and a looseness in the fitting between the secondary and primary bar. While the twist-lock clip could easily be replaced in this occurrence, the Applicant has developed a clip and a method for fitting it to the primary and secondary bar which provides greater contact area with the primary bar and the method of fabricating same eliminates or greatly reduces the three common problems associated with sparking erosion which contributes to a much tighter and secure latching mechanism, but one which is easily releasable by the user.

OBJECTS OF THE INVENTION

It is an object of the present invention to provide for a novel dental implant attachment for securing the artificial teeth portion of a dental prosthesis to the underlying support structure.

It is a further object of the present invention to provide a novel dental implant attachment which provides for greater contact area between the artificial teeth portion and the underlying support structure of a dental prosthesis.

It is a still further object of the present invention to provide for a novel dental implant attachment which is slidably securable between the artificial teeth portion and the underlying support structure of a dental prosthesis.

It is a still further object of the present invention to provide for a novel method for fabricating a latch attachment for securing the artificial teeth portion and the underlying support structure of a dental prosthesis.

It is a still further object of the present invention to provide for a novel method of fabrication of a dental attachment for a dental prosthesis which ensures that the attachment maintains intimate contact with the elements to which it is secured.

SUMMARY OF THE INVENTION

A slide latch attachment for securing the artificial teeth portion of a dental prosthesis to the underlying support structure, the slide latch attachment slidably secured in proximate the same plane and axis as the dental prosthesis and fabricated by the electric discharge method using the actual slide attachment as the final electrode for forming the channel for its receipt between the secondary support bar supra structure and underlying primary support structure.

BRIEF DESCRIPTION OF THE DRAWINGS

The objects and advantages of the present invention as well as other objects and advantages will become evident upon consideration of the drawings wherein:

FIG. 1 is a perspective exploded view of a lower jaw with a fixed removable implant system;

FIG. 2 is a bottom view of the supra structure further illustrating the secondary support bar;

DETAILED DESCRIPTION OF THE DRAWINGS

Figure 3:
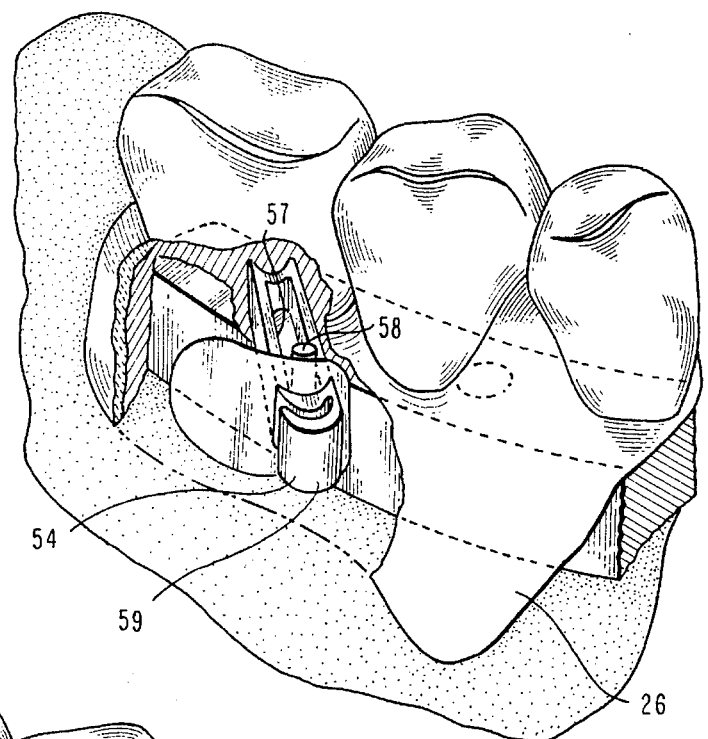
FIG. 3 is an enlarged cutaway view of the latching mechanism.

Referring to FIG. 1, there is illustrated a perspective exploded view of a fixed removable implant prosthesis in order to provide background for the present invention. There is illustrated, the alveolar bone 10 disposed within the jaw 12 with the upper portion of the jaw defined by the gum line 14. The dental prosthesis consists of a support structure 16 comprising a precision cast bar anchored in the alveolar bone 10 by means of a plurality of screws 17 which extend downwardly from the precision cast support structure 16 through abutments 18. Abutments 18 are surgically implanted into the alveolar bone. The screws or securing means 17 are recessed in precision cast support structure 16 such that supra structure 20 comprising the secondary bar having a plurality of internally-depending detentes 22 fit within the recesses of the precision cast support structure 16. In final form, the artificial teeth 24 and labial flare 26 are secured to the supra structure. The means for securing the supra structure to the precision cast bar has in the past comprised a latch or clip formed on the opposing ends of the supra structure and cooperable with the underlying support structure. These latches or clips were normally placed or formed on the interior, rear, opposing ends of the supra structure.

In order to better understand the relationship between the support structure 16 and the supra structure 20, reference is had to FIG. 2 which is a bottom perspective view of the supra structure 20. Supra structure 20 is arcuate in shape as a result of the fabrication process as described in U.S. Pat. No. 4,931,016. The supra structure is coincidental with the shape of the support structure 16 having a substantially flat inner top surface 30 and tapered interior sidewalls 32 and 34 to coincide with the tapered sidewalls of the precision cast support structure 16. Supra structure 20 has at least one guide post 36 for cooperation with a coincidental aperture 38 in precision cast support structure 16. Preferably, there would be more than one guide post cooperable with apertures in the support structure. The cooperation between these guide posts and the apertures in the support structure provide for a secure fit between the supra structure and support structure so as to prevent lateral displacement between the two.

While lateral displacement between the supra structure and the support structure is solved by the spark erosion fabrication process and the cooperation between guide pins and apertures in the supra structure and support structure, respectively, the dental technician, on behalf of the end user, must still ensure that the supra structure will be secured to the support structure such that there will be no vertical displacement between the supra structure and the support structure, particularly during the eating process. Applicant has developed an attachment means which provides for greater contact area between the attachment means and the support structure and the supra structure in order to maintain them in a vertically secure manner and Applicant has also developed a procedure which ensured the close tolerances required in order to maintain a secure fit over a long period of time.

Referring back to FIG. 1, there is illustrated an aperture 50 on the labial flare 26 of the artificial teeth portion of the prosthesis. This aperture 50 is the opening for a channel which is formed through the labial flare, through the supra structure (not shown) and into the support structure 16 at 52. This area in FIG. 1 is shown in a blow-up view in FIG. 3.

In FIG. 3, the area surrounding aperture 50 in labial flare 26 has been cut away to illustrate the manner in which the supra structure 20 is secured to support structure 16 by way of securing latch pin 54. Latch pin 54 is secured within a channel 56 which extends from the exterior of the labial flare 26 through the exterior wall 32 of the supra structure 20 and into the underlying support structure 16. This channel 56 as is formed at an acute angle to the arcuate axis of the support structure 16 and supra structure 20 so as to provide greater contact area between latch pin 54 and channel 56 as it extends into support structure 16. It is preferable to obtain as much contact area as possible. Thus, it will be recognized that the axis of the channel 56 as it approaches coincidental with the axis of the support structure 16 will provide the greatest contact area. Achieving this, preferable arrangement is dictated by the size of the prosthesis and its positioning within the mouth. Latch pin 54 thus secures the supra structure 20 and attached artificial teeth 24 in a secure manner to the support structure 16. The manner of achieving this secure fit by means of a tight frictional engagement between latch pin 54 and the sides of channel 56 as they extend into the support structure 16 is achieved by the fabrication method which will be described hereafter.

The purpose of the fixed removable implant is to allow an individual having a dental prosthesis the opportunity to remove the prosthesis for care and cleaning of the prosthesis as well as the underlying support structure and gums without the necessity of a dental visit. It is therefore desirable that the securing means which secures the artificial teeth and supra structure 20 to the underlying support structure 16 would be easily accessible to the prosthetic wearer as well as being secured in some manner such that it is not lost, swallowed or misplaced when the prosthesis is removed.

Applicant has addressed that problem in the instant matter by having a pin 58 formed on the supra structure and having latch pin 54 formed with a longitudinal slit 59 which would be cooperable with pin 58. In this manner, the prosthetic wearer can grasp the exterior clip 59 on latch pin 54 which is graspable with a fingernail on the exterior of the labial flare 26 and pull latch pin 54 outwardly disengaging it from the support structure 16, while at the same time limiting its outward motion by means of pin 58 so that latch pin 54 does not become disengaged from the supra structure 20. In this manner, the supra structure and accompanying artificial teeth can be removed for hygienic purposes.

Figure 4:
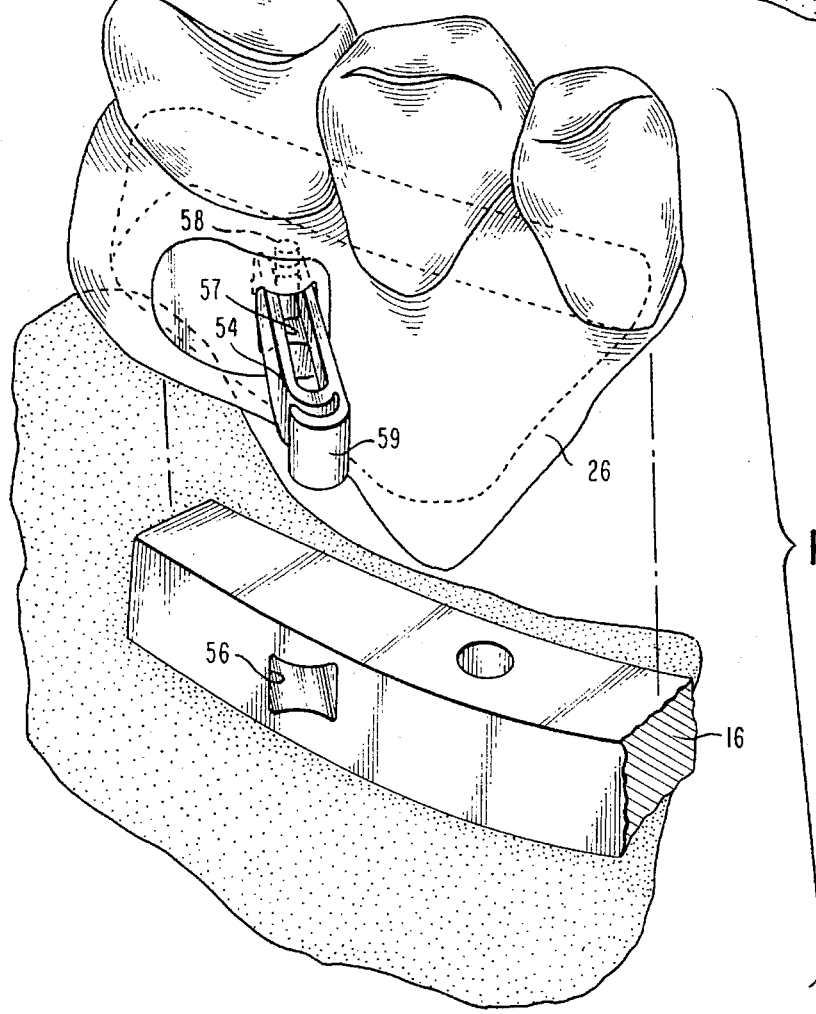
FIG. 4 is an enlarged, cutaway view of the latching mechanism in its removable state.

FIG. 4 is an exploded partial cutaway view of the same area illustrated in FIGS. 1 and 3. In FIG. 4, the latch pin 54 has been manipulated as discussed such that it extends outwardly from the supra structure and artificial teeth, but remains slidably secured thereto by means of pin 58. This has permitted the supra structure 20 and artificial teeth 24 to be lifted and removed from support structure 16.

The angle at which channel 54 is positioned in support structure 16 allows for a greater contact area between latch pin 54 and support structure 16 and thus improves the securing of the supra structure 20 and associated artificial teeth with the underlying support structure 16.

The manner in which channel 56 is positioned and fabricated overcomes the three basic problems associated with spark erosion, namely, overcut, taper, and squared corners. FIG. 5 is a schematic of the procedure for forming channel 54.

Figure 5A:
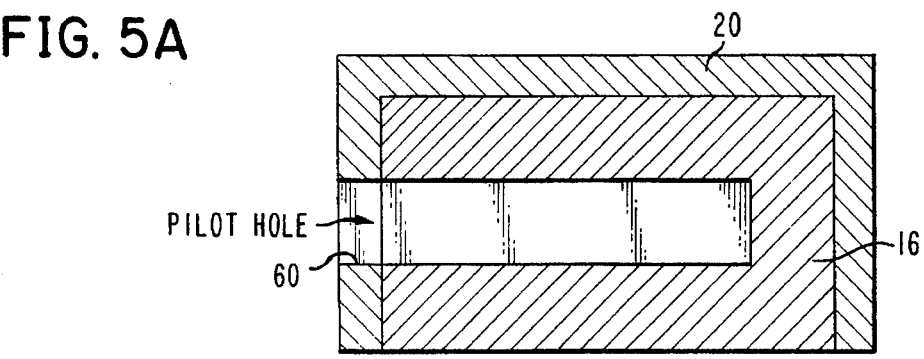
FIGS. 5A–5D show series of four (4) cross-sections illustrating the method of spark erosion in forming the channel for the attachment means.
Figure 5B:
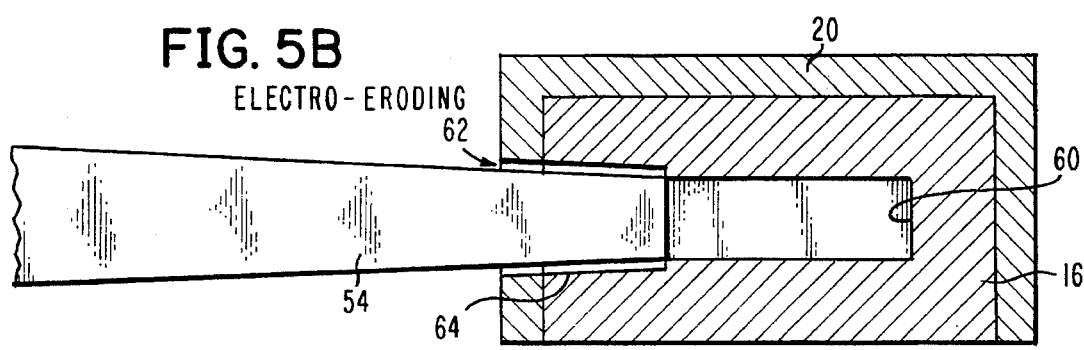
Figure 5C:
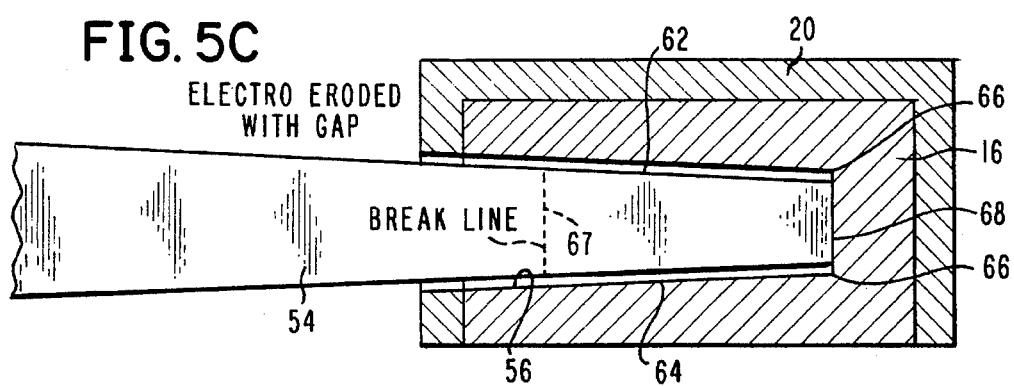

In FIGS. 5A–5D a cross-section of the support structure 16 and supra structure 20 in engaged relationship is illustrated. The initial step comprises the spark erosion of a pilot hole 60 from the exterior surface of the supra structure 20, through the sidewall of the supra structure 20 and into support structure 16 (FIG. 5A). The pilot hole is formed with an electrode having a circumference or cross-section less than that of the latch pin 54. Once the pilot hole 60 has been formed, then the latch pin 54 itself is used as the subsequent electrode for expanding the size of the pilot hole via spark erosion to conform to the cross-section of the latch pin 54. As illustrated in FIG. 5B, the problem with overcut, the continued erosion of material along the axis of the electrode is evident at 62. The additional problem of tapering of the channel as a result of overcut is also identifiable at 64 (FIG. 5C). These problems are overcome by fabricating latch pin 54 in a slightly tapered configuration as will be discussed with respect to FIG. 5.

Figure 5D:
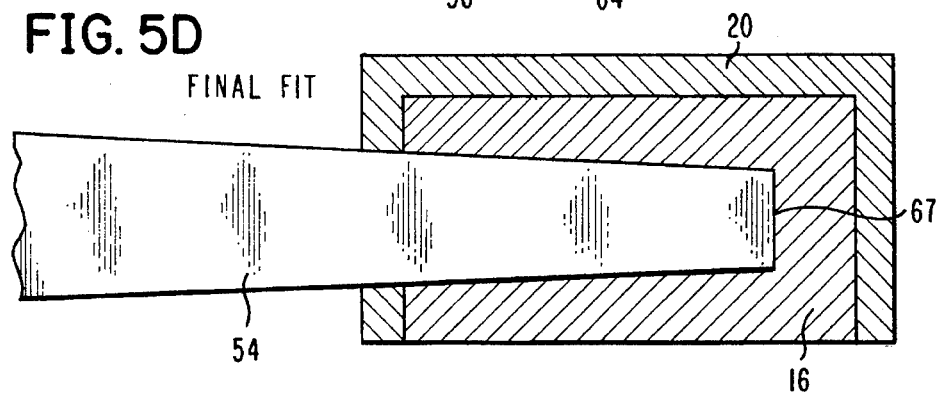

FIG. 5D illustrates the complete spark erosion of the pilot hole 60 by latch pin 54 utilized as an electrode. The overcut and taper are evident along the entire channel 56 and the third problem with spark erosion, namely the inability to obtain squared corners at the butt end of the recess because of higher concentration of flux or discharges at the corner of the electrode are now evident at 66.

These problems can now be alleviated so as to ensure that latch pin 54, which has been utilized as the electrode in forming channel 56 can have surface to surface contact between its entire periphery and the interior walls of channel 56. This is illustrated in FIG. 5 in which after channel 56 has been formed by spark erosion utilizing latch pin 54 as the electrode, latch pin 54 can be severed at a point 67, proximate to its forward tip 68. The butt end of latch pin 54 is now at point 67 and as a result of the taper of latch pin 54 being used as the electrode in the spark erosion process, the cross-section of latch pin 54 from butt end 67 rearwardly is greater than that of the former tip of latch pin 54 which was severed. As a result, the periphery of latch pin 54 now conforms to and is in intimate contact with the interior surface of channel 56 and its butt end 67 abuts the terminus of channel 56. Secure frictional engagement is thus achieved between latch pin 54 and channel 56.

The remaining fabrication processes associated with latch pin 54 would be to position or fabricate longitudinal slit 57 into latch pin 54 and form the exterior clip 62 onto latch pin 54. Thereafter, an aperture can be formed in the labial flare 26 of the artificial teeth so as to permit the extension of latch pin 54 to the exterior surface of the labial flare in order to be grasped by the denture wearer. It should be noted, however, that the fabrication of latch pin 54 may be accomplished prior to its use as an electrode for eroding pilot hole 60.

While the present invention has been described in connection with the exemplary embodiment thereof, it will be understood that many modifications will be apparent to those of ordinary skill in the art and that this application is intended to cover any adaptations or variations thereof. Therefore, it is manifestly intended that this invention only be limited by the claims and the equivalents thereof.

What is claimed is:

1. A dental prosthesis assembly, such as a denture, partial denture, crown, bridge or implant, said dental prosthesis assembly comprising:

a dental prosthesis having an underlying metal support, a removable supra structure and artificial teeth being overlaid and attached to said supra structure;

a holding element in the form of a latch pin, the latch pin having an inner end and an outer end, said latch pin having a decreasing cross-section from said outer end to said inner end, said latch pin having a slot on its longitudinal axis for retention of said latch pin to said supra structure and said artificial teeth, said latch pin having a removal clip at its outer end;

a receiving channel for said latch pin extending from the exterior surface of said overlaid teeth through said supra structure and terminating in said underlying metal support, said receiving channel having a cross-section complimentary to said cross-section of said latch pin, said latch pin slidably frictionally engageable with said receiving channel from a locked engaging position securing said supra structure and said artificial teeth to said underlying metal support, to a disengaged position, permitting the separation of said supra structure and said artificial teeth from said underlying metal support;

a stop pin formed in said supra structure cooperable with said slot of said latch pin to retain said latch pin in engagement with said supra structure when said supra structure and said artificial teeth are removed from said underlying metal support.

2. The dental prosthesis assembly in accordance with claim 1 wherein said slot in said latch pin comprises a slit aperture through said latch pin on its longitudinal axis for a portion of said longitudinal axis, said slit aperture cooperable with said stop pin formed in said receiving channel of said supra structure, said stop pin extending through said slit aperture in said latch pin and limiting the movement of said latch pin from a locked position securing said supra structure to said underlying metal support, to an unlocked position permitting the separation of said supra structure from said underlying metal support by retaining said latch pin on said supra structure.

3. The dental prosthesis in accordance with claim 1 wherein said slot in said latch pin comprises a longitudinal detente on a longitudinal side of said latch pin, said detente cooperable with a downwardly depending pin formed in said receiving channel of said supra structure, said downwardly depending pin cooperable with said detente to limit the movement of said latch pin from a locked position securing said supra structure to said underlying metal support, to an unlocked position permitting the separation of said supra structure from said underlying metal support, but retaining said latch pin on said supra structure.

4. The dental prosthesis in accordance with claim 1 wherein said receiving channel is formed in a horizontal plane in said artificial teeth, supra structure and underlying metal support, and said receiving channel is formed in a non-perpendicular angle to said artificial teeth, supra structure and said underlying metal support.

5. A method for the manufacture of a dental prosthesis, such as dentures, partial dentures, implants, crowns or bridges, and the retention of same within the mouth, wherein there is included a preformed underlying metal support, a preformed supra structure and artificial teeth overlaid and attached to said supra structure with at least one releasable holding element, the method comprising the steps of:

a) fitting the preformed supra structure on the underlying metal support;

b) forming a guide bore by means of sparking erosion from the exterior of said supra structure through said supra structure and into said underlying metal support;

c) forming a receiving bore for a releasable holding element having an inner end and an outer end, and having a tapered cross-section from said outer end to said inner end, said receiving bore formed by sparking erosion utilizing said guide bore as a guide, and using said releasable holding element as the electrode for said sparking erosion;

d) trimming said inner end of said releasable holding element after accomplishing the formation of said receiving bore by sparking erosion to compensate for sparking erosion over cut and ensuring said inner end of said releasable holding element is flush with the end of said receiving bore;

e) forming a securing means on said releasable holding element to maintain said releasable holding element to said supra structure;

f) forming a removal clip on said outer end of said releasable holding element; and g) forming an aperture in said overlaying artificial teeth to allow access to said removal clip by a dental prosthesis user.

6. The method in accordance with claim 5 wherein said step of forming said securing means comprises the step of forming a slot aperture on the longitudinal axis of said releasable holding element cooperable with a pin in said receiving bore of said supra structure to retain said releasable holding element to said supra structure.

7. The method in accordance with claim 5 wherein said step of forming said securing means comprises the step of forming a detente along a longitudinal side of said releasable holding element, said detente cooperable with a pin in said receiving bore of said supra structure to retain said releasable holding element to said supra structure.

\* \* \* \* \*